(12) United States Patent
Fujii et al.

(10) Patent No.: US 6,609,826 B1
(45) Date of Patent: Aug. 26, 2003

(54) MOBILE RADIOGRAPHY DEVICE

(75) Inventors: Shigeo Fujii, Kyoto (JP); Kouichiro Oku, Kyoto (JP); Yoshitomo Tsukamoto, Osaka (JP); Minoru Tanaka, Nara (JP); Atsushi Ninomiya, Tokyo (JP); Ryosuke Fukami, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 10/048,713

(22) PCT Filed: Aug. 4, 2000

(86) PCT No.: PCT/JP00/05243
§ 371 (c)(1),
(2), (4) Date: Apr. 24, 2002

(87) PCT Pub. No.: WO01/10300
PCT Pub. Date: Feb. 15, 2001

(30) Foreign Application Priority Data

Aug. 6, 1999 (JP) .............................................. 11-223484
Nov. 26, 1999 (JP) .............................................. 11-336008
Apr. 3, 2000 (JP) .............................................. 2000-101459

(51) Int. Cl.[7] .................................................. H05G 1/02
(52) U.S. Cl. ......................................... 378/198; 378/197
(58) Field of Search ................................ 378/195–198

(56) References Cited

U.S. PATENT DOCUMENTS 4,802,197 A * 1/1989 Juergens ..................... 378/198
5,583,909 A * 12/1996 Hanover ..................... 378/198
6,120,180 A * 9/2000 Graumann .................. 378/198

* cited by examiner

Primary Examiner—Craig E. Church
(74) Attorney, Agent, or Firm—Antonelli, Terry, Stout & Kraus, LLP

(57) ABSTRACT

A mobile type radiography apparatus having a truck movable on a floor, an X-ray control unit mounted on the truck, a first supporting arm having two branches supporting an X-ray generator and an X-ray image reception device at mutually opposite positions to sandwich a subject between the X-ray generator and the X-ray image reception device, an arm supporting mechanism having a second arm extending toward an outside of the branches of the first supporting arm and supporting the first supporting arm so as to be movable. A supporting pole mechanism is mounted on the truck so as to extend upwardly therefrom and an arm motion mechanism is located between the arm supporting mechanism and the supporting pole mechanism for linearly supporting the arm supporting mechanism so as to enable movement of the first supporting arm in horizontal directions perpendicular to longitudinal directions of the second arm.

17 Claims, 14 Drawing Sheets

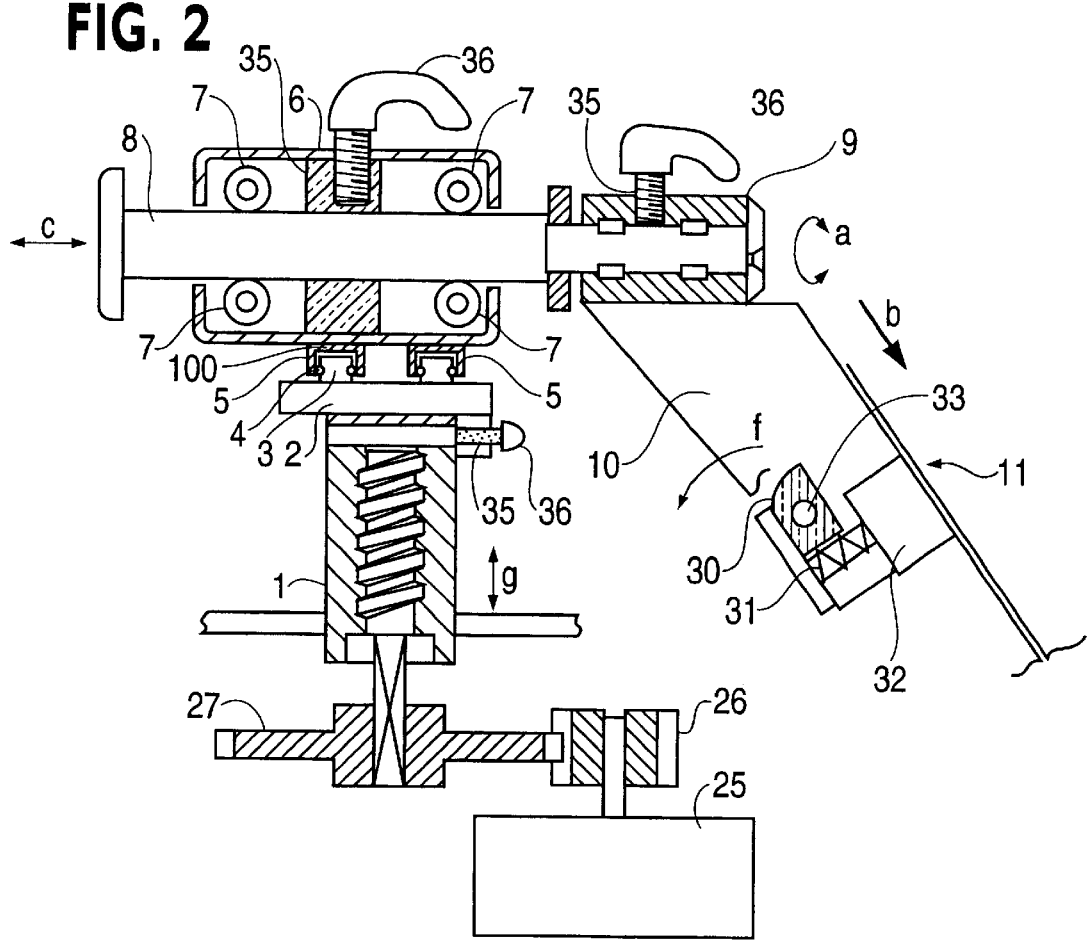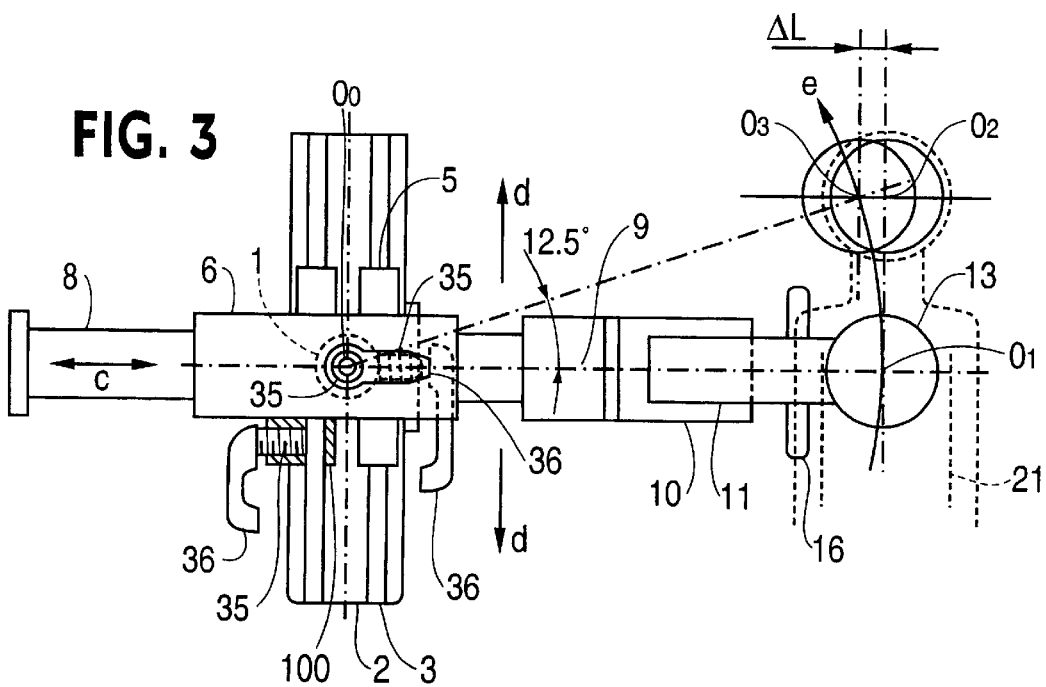

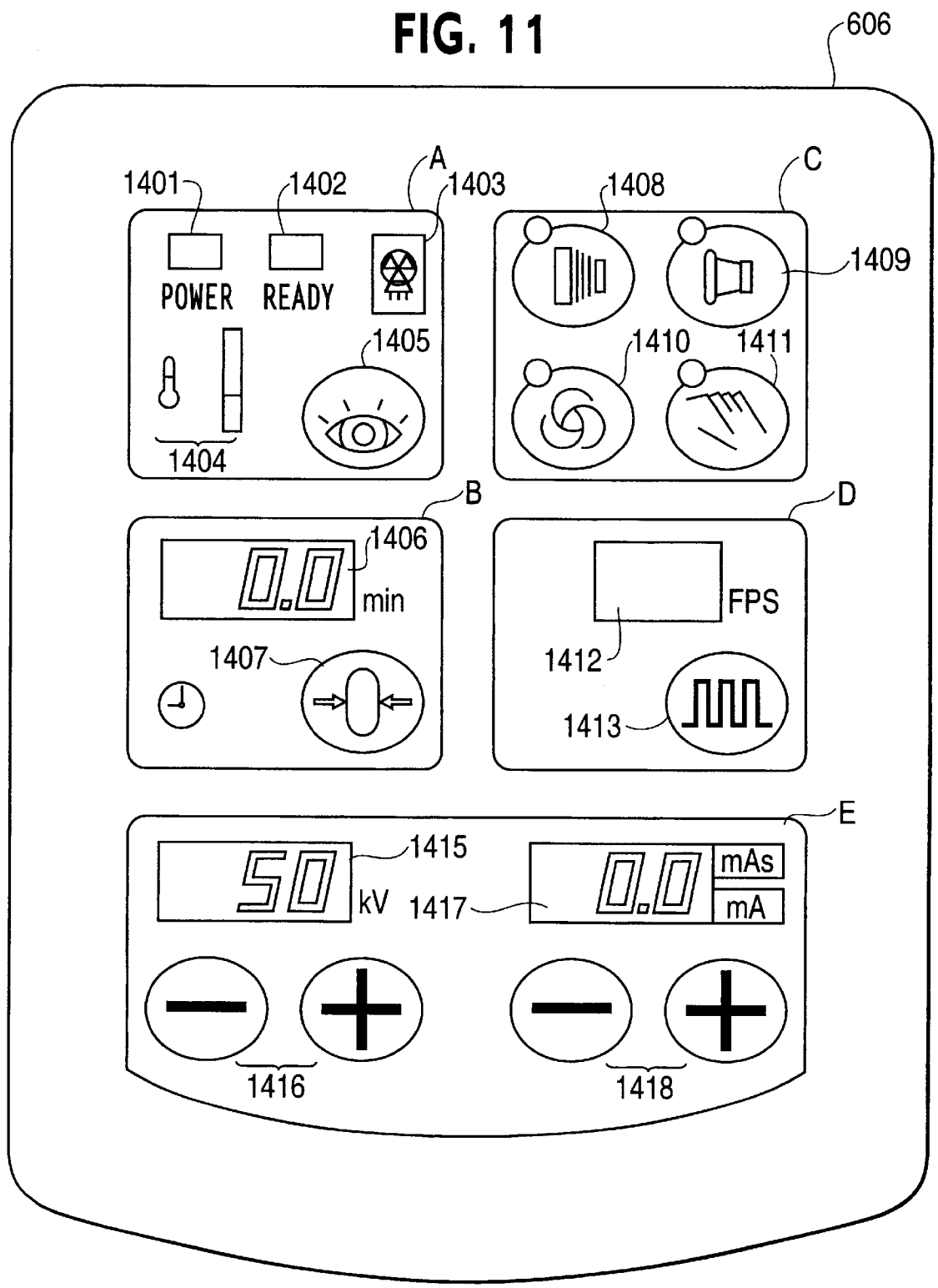

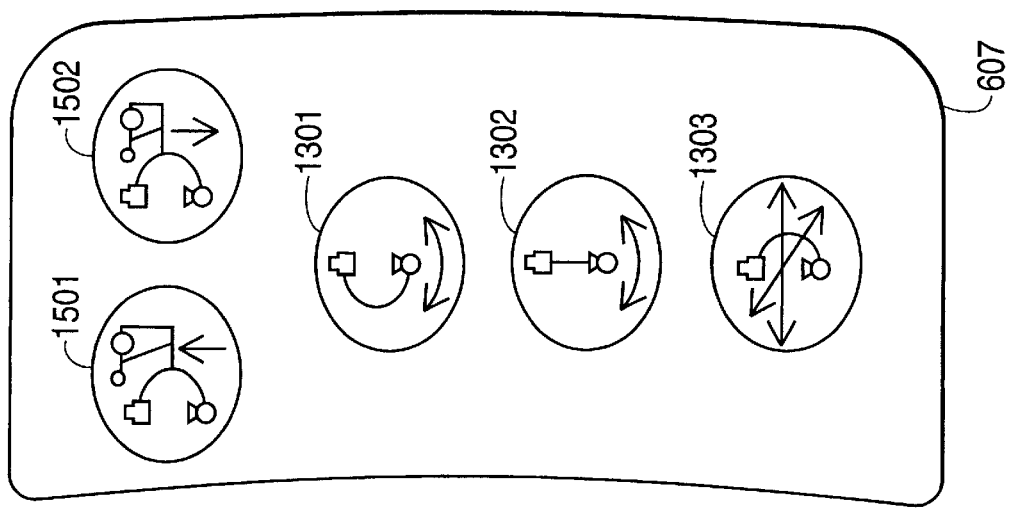
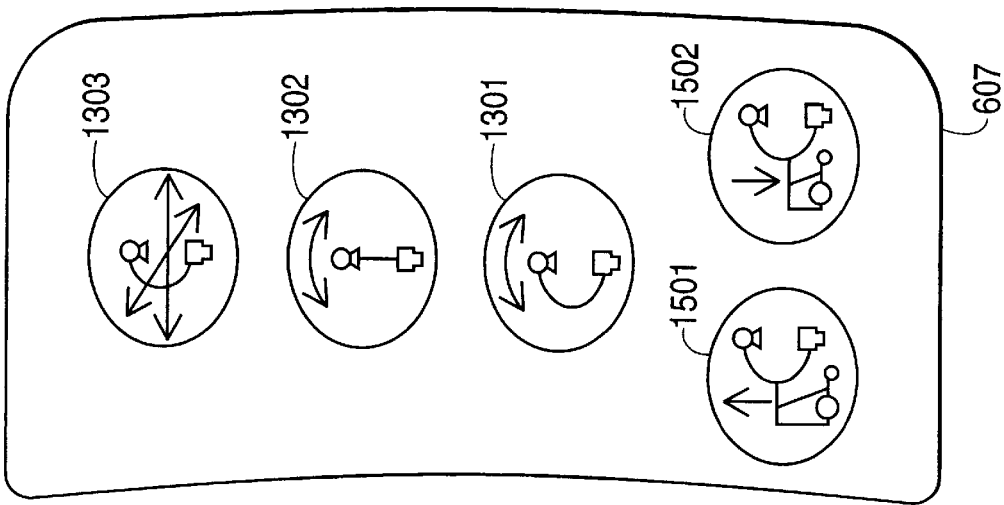

MOBILE RADIOGRAPHY DEVICE

FIELD OF THE INVENTION

This invention relates to a mobile type radiography apparatus including an X-ray apparatus mounted on a moving truck to perform fluoroscopy and/or radiography by transporting the X-ray apparatus into a surgery room, and especially to a mobile type radiography apparatus suitable for performing examination or treatment by inserting a catheter into an object to be examined under observation of image.

BACKGROUND OF THE INVENTION

The above mobile type radiography apparatus is a fluoroscopic and radiographic system capable of fluoroscopy or radiography for examination or surgery support by transporting the apparatus to a surgery room with a moving truck. In this system, an X-ray tube device (most of them are a mono-tank type integrally formed so as to include a high voltage generator and an X-ray collimator) is mounted on one end of a semi-circle type arm, i.e. so-called C-arm. An X-ray image reception device including, for example an image intensifier (hereinafter referred to as I.I.) and a television (TV) camera, is mounted on another end of the C-arm. The X-ray tube device and the X-ray image reception device are mounted on the C-arm so as to face each other for balancing the weight to acquire smooth and free motion of the X-ray tube device and the X-ray image reception device can be properly registered with an imaging part of the subject.

In the conventional mobile type radiography apparatus, a C-arm motion mechanism for registering the X-ray tube device and the X-ray image reception device supported by the C-arm with a part of subject subjected to fluoroscopy or radiography has a C-arm vertical motion mechanism for moving the C-arm and the X-ray tube device and the X-ray image receiving device, both supported by the C-arm (hereinafter referred to as an entire C-arm) in the vertical directions, a revolving mechanism for rotating the center of the entire C-arm around a rotation axis, of which direction is perpendicular to the longitudinal axial direction of the subject, a C-arm circular motion mechanism for rotating the C-arm along the arc, an C-arm swing mechanism for driving the entire C-arm to swing in the horizontal direction around the vertical motion axis, a C-arm front/back motion mechanism for forward and backward driving a central portion of the entire C-arm in the directions perpendicular to the longitudinal axial direction of the subject.

Although the mobile type radiography apparatus is most frequently used in the field of orthopedic surgery, it is also used in other fields because of their convenient movable feature advantageous for both of fluoroscopy and radiography.

For example, the mobile type radiography apparatus is used also in angiography's field of head. Moreover, it is used in a treatment without incision to the body of the subject under an X-ray image observation (i.e. so-called Interventional Radiology, hereinafter referred to as IVR).

Such examination and treatment are to examine a thrombus or a contraction rate of vessels in a head, and to treat by dissolving the thrombus and enlarging contracted vessels. Therefore, it is necessary to insert a catheter for injecting a contrast medium and a solution for dissolving thrombus to the head vessel, and for inserting an instrument for enlarging the contracted vessels smoothly into the diseased part of the head while observing X-ray image.

In this case, it is necessary that the X-ray tube device and the X-ray image reception device supported by the C-arm are appropriately registered with the subject such that a fluoroscopic image of the catheter is displayed inside a monitor to catch the traveling of the catheter for guiding the catheter to the diseased part while identifying the location of the catheter with the mobile type radiography apparatus. This positioning method in a conventional apparatus will be explained in reference of FIGS. 4($a$) and 4($b$).

FIG. 4($a$) is a perspective view showing relationship between the entire C-arm and the subject when the X-ray tube device and the X-ray image reception device are registered at a catheter inserting point $O_1$ at a time of inserting a catheter from a vessel of heart.

First, a subject is laid with its back on a surgery bed. Then, the truck is positioned such that the C-arm of the X-ray device surrounds the subject on the surgery bed between the X-ray tube device 12 and X-ray image reception device 13 and a catheter inserting point $O_1$ is located between X-ray tube device 12 and X-ray reception device 13. In use of a C-arm vertical motion mechanism, a center of X-ray irradiating field of the X-ray tube device is registered to coincide with the point $O_1$. This registration is performed by properly using a revolving mechanism, a circular motion mechanism, a front/back motion mechanism in addition to the vertical motion mechanism. Point $O_0$ in FIG. 4($a$) designates a center of swinging axis of the C-arm swing mechanism for swinging the entire C-arm from left to right in the horizontal directions, and reference R designates a radius of the swinging locus.

Next, when a doctor inserts the tip of catheter from point $O_1$ in FIG. 4($a$) to point $O_2$ in FIG. 4($a$) or FIG. 4($b$), being a diseased part (target of the treatment) of subject 21, the C-arm is moved by its swing motion under observation of fluoroscopic image of the catheter with the above C-arm swing mechanism. Then X-ray tube device 12 and X-ray image reception device 13, which are installed in the C-arm, are moved to point $O_3$ in FIG. 4($b$) along a circumference of swinging radius R. However, the location of point $O_3$ differs from the location of target point $O_2$ by $\Delta L$. Therefore, the correction of location is required as much.

Thus using the C-arm front/back motion mechanism, the location of the entire C-arm is moved from point $O_3$ to point $O_2$, and the location of $\Delta L$ is corrected so that an irradiation center of X-ray tube device 12 corresponds with the target point $O_2$.

Another positioning method is to register by moving the truck of C-arm in pursuit of traveling of the catheter tip from point $O_1$ to point $O_2$. However, because the weight of the entire apparatus mounted on this truck is 200 kg or more including the truck itself, it is hard to register by moving the truck (especially in a case where an operator is female). Either, in the case where the truck is moved to the small diseased part of the head vessels, sufficient accuracy of the registration is scarcely obtained. Therefore, the final and delicate registration should be conducted with the C-arm swing mechanism and the C-arm front/back motion mechanism.

As described, in the registration using the front/back motion or the combination of the swing mechanism and the front/back motion mechanism, a substantial time is necessary for the registration, whereby a time for fluoroscopy is elongated and an exposed amount of X-ray to a patient is increased.

Since the conventional mobile type radiography apparatus is designed so as to be used for orthopedic surgery as described above, an operation unit of the apparatus is placed on the top of the X-ray control unit, mounted on the truck. The arrangement of the operation unit is far away from an interconnecting line between the X-ray tube device and the X-ray image reception device. In a case of orthopedic surgery, even if the operation unit is located away from the line, there is no operational problem as long as the location of the X-ray tube device and the X-ray image reception device are not changed after these devices are once positioned for radiography. But when the tip of catheter is chased for imaging as in the above IVR, because the operation units has to be operated frequently, there is a problem that the unit is operated with difficulty when the control unit is positioned far away.

Furthermore, in the conventional mobile type radiography device, a cable for connecting the X-ray tube device with X-ray image reception device installed in the C-arm were wired on the outside of the C-arm to keep slack for enabling the C-arm rotation. Accordingly, there is a risk that the cable possibly is an obstacle to footstep of a doctor when he or she performs an IVR method in use of the mobile type radiography device, because the cable moves on a floor of surgery room when the apparatus is moved along with the moving of catheter tip.

The first object of the present invention is to provide a mobile type radiography apparatus suitable for performing an IVR method in reference to the above problems.

The second object of the present invention is to provide a mobile type radiography apparatus capable of performing fluoroscopy while chasing a catheter tip inserted in and moving through a subject to be examined when a doctor performs an IVR method.

The third object of the present invention is to provide a mobile type radiography apparatus having an operation unit suitable for performing an IVR method.

The forth object of the present invention is to provide a mobile type radiography apparatus, wherein a cable connecting an X-ray tube device with an X-ray image reception device is not obstacle to a doctor who performs an IVR method.

SUMMARY OF THE INVENTION

To solve the above object in the present invention, the mobile type radiography apparatus comprises a C-arm motion mechanism for linearly moving an entire C-arm in a longitudinal direction of a surgery bed under a state that a moving truck is positioned at a predetermined position with respect to the surgery bed; an operation unit arranged in a position where a doctor or the like can operate this when he or she stands in the vicinity of the C-arm; a cable for connecting an X-ray tube device with an X-ray image reception device, which cable accommodated in an inside of the C-arm; and a cable handling mechanism capable of respectively winding up and drawing out cables connected to the X-ray tube device and the X-ray image reception device in accordance with a circular motion of the C-arm.

BRIEF DESCRIPTION OF THE DRAWINGS

FIG. 2 is a cross-sectional view taken along line A—A in FIG. 1.

FIG. 3 is a plan view of the C-arm motion mechanism.

FIG. 11 is a view for explaining an arrangement and a display of operation buttons positioned on a protruding portion of the panel shown in FIG. 9.

FIG. 12 is a view for explaining an arrangement and a display of operation buttons in an operation panel disposed in the C-arm supporting part.

BEST MODE FOR CARRYING OUT THE INVENTION

Figure 1:
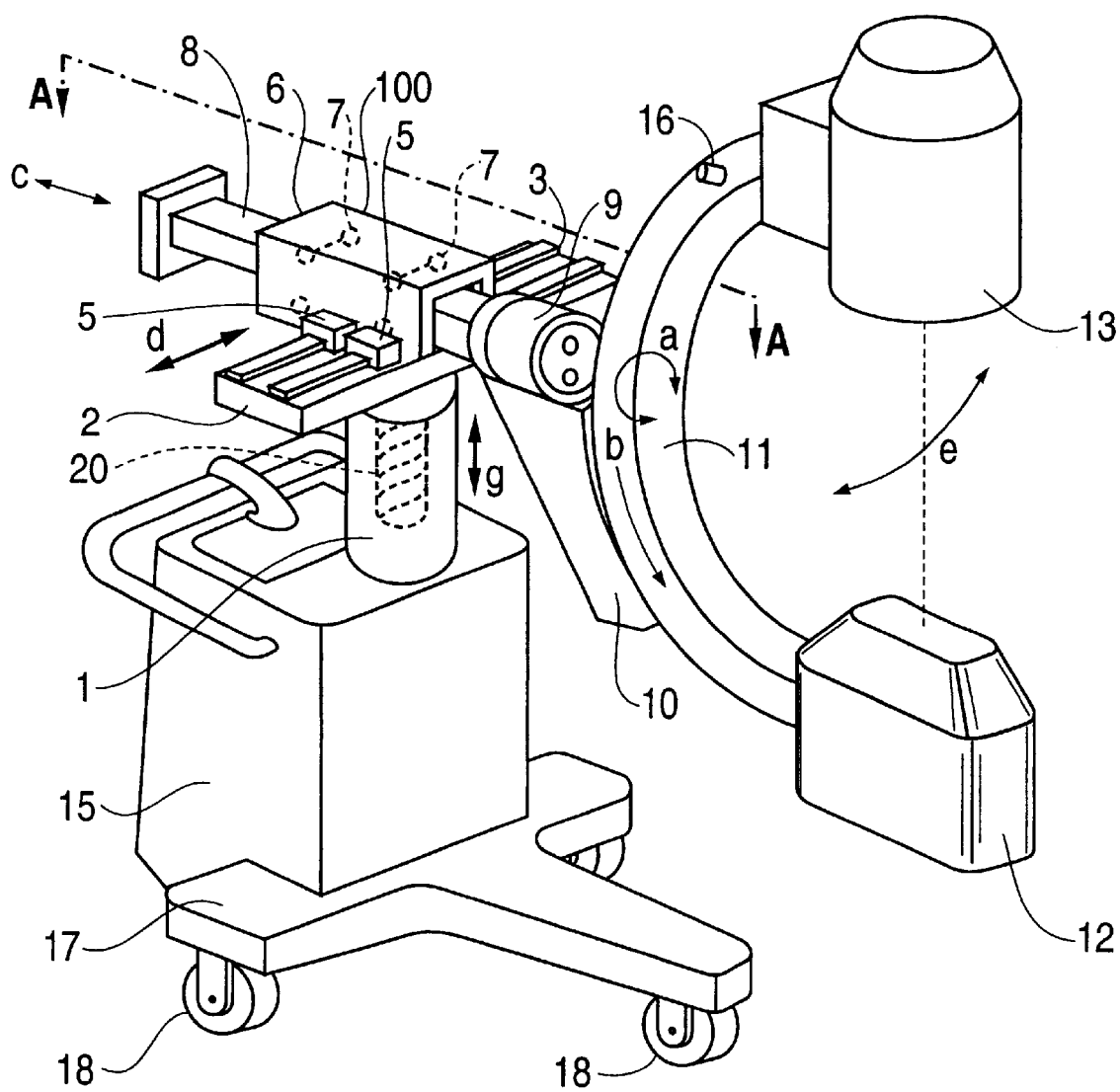
FIG. 1 is a perspective view illustrating a C-arm motion mechanism of the mobile type radiography apparatus according to the present invention.

Hereinafter, a mobile type radiography apparatus according to the present invention will be described in detail in reference of the figures. FIG. 1 illustrates an interior structure of the mobile type radiography apparatus according to the present invention in a state that its cover is removed. As shown in FIG. 1, the mobile type radiography apparatus comprises X-ray tube device 12, X-ray image reception device 13 having X-ray television device including I.I., C-arm portion 11 for supporting X-ray tube device 12 and X-ray image reception device 13 respectively at its ends, registering mechanism portion 100 (C-arm motion mechanism portion) for registering X-ray tube apparatus 12 and X-ray image reception device 13 at various fluoroscopic or imaging positions of the subject to be examined by moving the entire C-arm, comprising X-ray tube device 12, X-ray image reception device 13, and C-arm 11 as described above, and a main frame 15 accommodating a high voltage generator for generating a high voltage to be applied to the X-ray tube of the X-ray tube device and an X-rays control part or the like, controlling start and stop of X-ray irradiation generated by an X-ray source and X-ray irradiating conditions, and truck 17 having casters 18 enabling movement of the entire C-arm and registering mechanism portion 100 and main frame.

A mobile type X-ray TV apparatus for surgery according to the present invention includes the following motion mechanisms for respectively registering X-ray tube device 12 and X-ray image reception device 13 by moving the C-arm to various fluoroscopic or imaging positions.

Next, the composition and motion of these motion mechanisms will be described in detail in reference of FIG. 1 to FIG. 3. Mean while, FIG. 2 is a cross-sectional view taken along line A—A in mechanism portion 100 shown in FIG. 1. FIG. 3 shows a plan view of mechanism 100 in FIG. 1.

(1) C-arm Vertical Motion Mechanism

The C-arm vertical motion mechanism includes main pole 1 for registering the center of X-ray irradiating field from X-ray tube device 12 with a fluoroscopic and imaging position of a subject and for lifting up and down the entire C-arm to set a distance between the focus of the X-ray tube accommodated in an interior of X-ray tube device 12 and the subject, screw 20 located inside the main pole 1, motor 25 being a power source for lifting up and down the entire C-arm, pinion 26 fixed to an output axis of motor 25 to transmit the rotating force of it, and gear 27 for reducing the revolution speed of motor 25 through pinion 26 and for transmitting rotating force generated by motor 25 to screw 20.

Main pole 1 ascends when screw 20 is rotated (clockwise revolution when reviewed from gear 27), and main pole 1 descends when screw 20 is rotated in the reverse direction (directed by arrow g).

Ascent and descent of the C-arm by the mechanism are performed by operating an ascending switch and a descending switch which are arranged in an operation unit to be described below. The C-arm ascends when the ascending switch is closed. The C-arm descends when the descending switch is closed. When the ascending switch is closed, motor 25 rotates in the counter-clockwise direction. Revolution force is transmitted from pinion 26 to gear 27, further from gear 27 to screw 20. Screw 20 is engaged with a female screw (not shown) formed inside main pole 1. Screw 20 rotates in the advancing direction, main pole 1 ascends along with the C-arm. On the other hand, in order to descend the C-arm, the descending switch is closed. Then, motor 25 revolves in the clockwise direction, and the revolution force is transmitted from pinion 26 to gear 27 and further from gear 27 to screw 20, whereby screw 20 rotates in a direction adverse to the ascending direction, and main pole 1 descends to simultaneously fall the C-arm.

(2) C-arm Revolution Mechanism

A C-arm revolution mechanism includes horizontal rotation bearing 9 supported by a shaft formed in agreement with C-arm front/back motion axis 8, C-arm supporting portion 10 for revolving in the direction of arrow in the figure, the C-arm supporting portion being integrally formed with this horizontal rotation bearing 9, screw shaft 35 forming a lock mechanism for fixing the revolution of C-arm at a revolving angle determined by registration, and handle 36 fixed to screw shaft 35.

The C-arm revolution motion in the mechanism is such that screw shaft 35 is released by rotating handle 36 of a lock mechanism located in horizontal rotation bearing 9 to release pressure of a tip of screw shaft 35 on the shaft for freeing the fixation of the horizontal rotation bearing; and the C-arm is revolved by manually pressing handle 16 formed on the C-arm or vicinity thereof in the direction of arrow a in the figure. After registering the C-arm by revolving the C-arm by a predetermined degree, handle 36 is rotated in the reverse direction, and the C-arm is fixed so as not to revolve by said screw shaft 35 of said rock mechanism.

(3) C-arm Circular Motion Mechanism

A C-arm circular motion mechanism includes C-arm support part 10 explained in the above C-arm revolution motion mechanism, C-arm 11, C-arm guide mechanism (not shown) formed in C-arm supporting portion 11, and a lock mechanism formed in C-arm supporting portion 10. The lock mechanism for this circular motion includes cam 30 rotatably attached to C-arm supporting portion 10 through shaft 33 as shown in FIG. 2, and pad member 32 for generating braking force for stopping motion of C-arm 11, the pad member being urged by spring 31 to push C-arm 11 at its tip end.

The C-arm circular motion in the mechanism is such that the tip of pad 32 is detached from C-arm 11 by rotating cam 30 around shaft 33 in the direction of arrow in FIG. 2; and C-arm 11 is moved along a circular arc in the direction of arrow b while manually holding handle 16 or vicinity thereof. After finishing setting an X-ray tube device and an X-ray image reception device at an imaging angle, cam 30 is rotated in the reverse direction, and the lock mechanism is activated.

(4) C-arm Swing Mechanism

Although C-arm swing mechanism is not illustrated in detail in the figure, it includes a swing shaft formed in an upper portion of main pole 1 so as to be in agreement with a central axis of the main pole, a bearing box formed inside base 2 of left/right motion mechanism to be described below, a bearing accommodated in the bearing box, and a lock mechanism including screw 35 and handle 36, both located in a part of base 2.

In thus constructed C-arm swing mechanism, screw shaft 35 for locking movement between the above swing shaft and base 2 is released by rotating with handle 36. Accordingly, by pressing handle 16 or vicinity thereof, C-arm 11 can be revolved in the direction of arrow e around the central axis of main pole 1.

(5) C-arm Front/back Motion Mechanism

C-arm front/back motion mechanism includes housing 6, four pairs of bearing 7 for front/back motion to guide front/back motion axis 8 disposed in the interior of housing 6, and a lock mechanism for locking traveling of front/back motion axis 8. The lock mechanism includes screw axis 35 and handle 36, wherein the member for receiving screw shaft 35 is located inside housing 6.

In the above described front/back motion mechanism, lock of front/back motion shaft 8 is released by rotating to relax screw shaft 35 located on an upper surface of housing 6 with handle 26, and C-arm 11 is moved in the front/back direction of arrow c by pushing handle 16 installed on a side surface of C-arm 11 or vicinity thereof. Further, a minute front/back motion may be realized such that a rack is formed on the front/back shaft; a rotational shaft is formed in housing 6; and a pinion is attached to the shaft to enable manual rotation of the rotational shaft.

Although, in the above, the C-arm revolution mechanism, the C-arm circular motion mechanism, the C-arm swing mechanism, and the C-arm front/back motion mechanism have been explained so that these are manually operated, all of these may be electrically operated. The electrical operation can be achieved by appropriately using a motor, a gear mechanism, a screw mechanism, and a belt mechanism.

Hereinafter, a C-arm left/right motion mechanism according to the present invention will be described in detail.

(6) C-arm Left/right Motion Mechanism

FIG. 3 is a plan view of the entire C-arm and the C-arm left/right motion mechanism, obtained by viewing in the downward vertical direction. In FIGS. 2 and 3, numerical reference 2 designates a left/right motion base. Numerical reference 3 designates a pair of linear guide rails fixed on an upper surface of base 2 with a predetermined distance. Numerical reference 4 designates a rolling element engaged with a guide groove formed in the longitudinal direction of guide rail 3 so as to rotate and be in contact with the guide rail. Numerical reference 5 designates a pair of housings engaged with guide rail 3 through rolling elements 4 and holding the rolling elements 4. A linear motion guide includes guide rail 3 and rolling elements 4, and housing 5. The moving direction of the linear motion guide are set in the horizontal direction perpendicular to front/back motion axis 8 of the C-arm front/back motion mechanism.

The C-arm left/right motion mechanism has a lock mechanism in one of the housings as in FIG. 3. The lock mechanism includes screw shaft 35 and handle 36, wherein rotating handle 36□ screw shaft 35 pushes a side of the guide rail to generate stopping force. This function is the same as that in the above described various mechanisms.

In this C-arm left/right motion mechanism, by rotating handle 36 to release screw shaft 35 located in housing 5, lock between housing 5 and guide rail 3 is canceled. Under this condition, by pushing handle 16 shown in FIG. 1 in the direction d shown in the figure, rolling elements 4 held in the grooves are in contact with guide rail 3 and housing 5 and rotate, whereby housing 5 travels on and along guide rail 3. Thus the entire C-arm is moved in the horizontal directions. At this time, since guide rail 3 and housing 5 are in contact with the rotating rolling elements, force for operation can be small.

Next, an example of utilizing the remarkable effect of the C-arm left/right motion being the characteristic of the present invention will be described. The example is to insert a catheter at around a heart toward a diseased part of the head while observing the catheter to check and cure head vessels. Specifically, the example is to insert the catheter from point $O_1$ in FIG. 3 to the vessel of a subject, and to guide the catheter to the diseased part of the head vessels, i.e. point $O_2$ under observation of fluoroscopic image. In this case, the C-arm is registered according to the following procedure.

At first, the truck of the mobile type radiography apparatus is moved so that a subject to be examined in the spine body position on an operating table is interposed between the X-ray tube device and the X-ray image reception device, both supported by the C-arm, and at the position caster 18 for moving a surgical mobile type X-ray TV apparatus is located to prevent its movement. In this registration, the C-arm should be moved toward the viewer's side of FIG. 1 by the left/right motion mechanism, and roughly registered at the catheter inserting position. This is because a catheter is introduced from the heart of a subject to the head, and the C-arm surrounds the subject on the right side FIG. 3. In other words, it is necessary to change an initial setting position of the left/right motion mechanism depending on the inserting direction of the C-arm and the introducing direction of the chased catheter with respect to the subject, whereby there is an anxiety that an enough left/right motion stroke to chase the catheter is not maintained without keeping the stroke at the time of initial setting.

Next, the catheter is inserted into the subject. The X-ray center from X-ray tube device 12 is registered so as to be in agreement with point $O_1$ by adjusting to move and/or rotate the C-arm vertical motion mechanism, the C-arm revolution mechanism, the C-arm circular motion mechanism, the C-arm swing mechanism, the C-arm front/back motion mechanism and/or the C-arm left/right motion mechanism while observing fluoroscopic image of the tip position of the catheter inserted in the subject. Thus the preparation for chasing the catheter tip of the mobile type radiography apparatus is done. In addition, in this preparation, it is desirable that the C-arm left/right motion mechanism is set in a direction parallel to the axis of the subject to be examined. Because an X-ray irradiation field has an unignorable size, a catheter can be chased only by operating the C-arm left/right motion mechanism without operating motion mechanisms other than the left/right motion mechanism.

Next, the catheter is advanced to target point $O_2$ in the head vessel shown in FIG. 3. At this time, X-ray is constantly irradiated in accordance with the advance of catheter to observe the top of catheter. Further in use of the C-arm left/right motion mechanism, the catheter tip is chased while matching it with the X-ray irradiation center by linearly operating X-ray tube device 12 and X-ray image reception device 13 or operating the other motion mechanisms when necessary to finally guide the catheter tip to point $O_2$.

Further, the diseased part is checked and cured under a state that X-ray tube device 12 and X-ray image reception device 13 are registered with point $O_2$. Furthermore, when the target position is required to be changed, X-ray tube device 12 and X-ray image reception device 13 are appropriately registered with the changed target using the above-mentioned mechanism, and check and cure are done.

As described, by using the C-arm left/right motion mechanism according to the present invention, it is possible to linearly move the C-arm to the target position. Therefore, when the X-ray tube device and the X-ray image reception device are moved along a periphery of radius R of the swing motion by the C-arm swing motion, it is unnecessary to correct a difference between the target point and the moved point by operating the C-arm front/back motion mechanism, as required in the conventional mobile type radiography apparatus having the C-arm swing mechanism. Therefore, in the present invention, the registration time is shortened to thereby shorten the fluoroscopy time and reduce the exposed X-ray amount.

In addition, when the target position is $O_3$, the use C-arm swing mechanism occasionally works better than the C-arm left/right motion mechanism. If the C-arm left/right motion mechanism is appropriately combined with the conventional positioning mechanism, or the C-arm left/right moving mechanism according to the present invention is adopted, an unnecessary positioning mechanism among the conventional positioning mechanisms may be omitted. The above positioning mechanisms can be effectively combined in accordance with a purpose of check and cure, and a diseased part. Although, in the embodiment of the present invention, the example of using the compact rolling bearings provided with a small moving resistance in the C-arm left/right motion mechanism has been described, the present invention is not limited thereto, and a slide bearing, a fluid bearing, a magnetic floating bearing or the like can be used.

Further, in the above motion mechanism, although the method of fixing a motion shaft or a motion member by a screw, i.e., locking mechanism, it is possible to adopt a method of fixing the motion shaft to a bearing by a belt or a gear or a method of releasing pressure generated by an electromagnetic magnet and a spring. Further, in the embodiment of the present invention, although the example using I.I. and TV camera as the X-ray image reception apparatus is described, a semiconductor-type flat panel 2-dimensional X-ray detector, recently attracting attention may be used, wherein the type of X-ray image reception apparatus according to the present invention is not specifically limited.

As described, although by providing the C-arm left/right motion mechanism in the mobile type radiography apparatus, capability of chasing the catheter is improved in the case of using the mobile type radiography apparatus in the IVR method, the present invention also has a merit of improving operability of using the mobile type radiography apparatus in the IVR method by considering an operation panel located on the conventional apparatus. Hereinbelow, an explanation will be given. The invention described below is an example of enabling all-directional movement of the C-arm, wherein a motion of various motion mechanisms of C-arm is controlled by an operation button in an operation unit for the motion mechanism of an electromotive type or by a manual operation through a motion grip.

Figure 5:
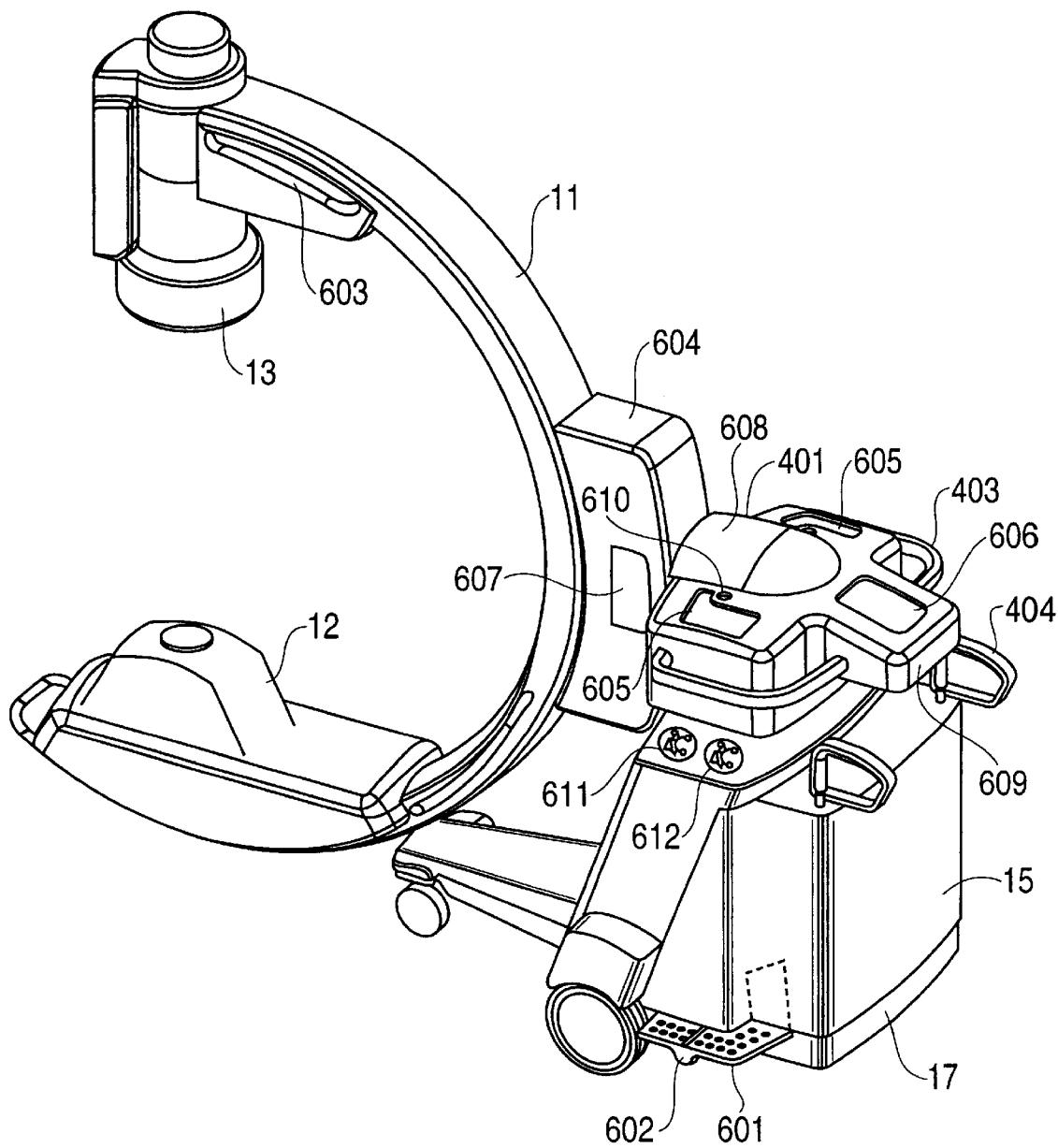
FIG. 5 is a perspective view illustrating an external view of an entire mobile type radiography apparatus according to an embodiment in the present invention.

FIG. 5 is an outside view of an apparatus constructed to have a cover and an operation unit on the mobile type radiography device having the mechanisms shown in FIG. 1. In FIG. 5, numerical reference 401 designates a front/back motion cover; numerical reference 403 designates a C-arm motion grip; numerical reference 404 designates a truck motion grip; numerical reference 601 designates a truck brake pedal; numerical reference 602 designates a pedal axis; numerical reference 603 designates a C-arm rotating grip; numerical reference 604 designates a support portion cover; numerical reference 605–607 designate operation panels, numerical reference 608 designates a bulge portion; numerical reference 609 designates a protruding portion; numerical reference 610 is an emergency button, and other codes are the same as those in FIG. 1.

Figure 6:
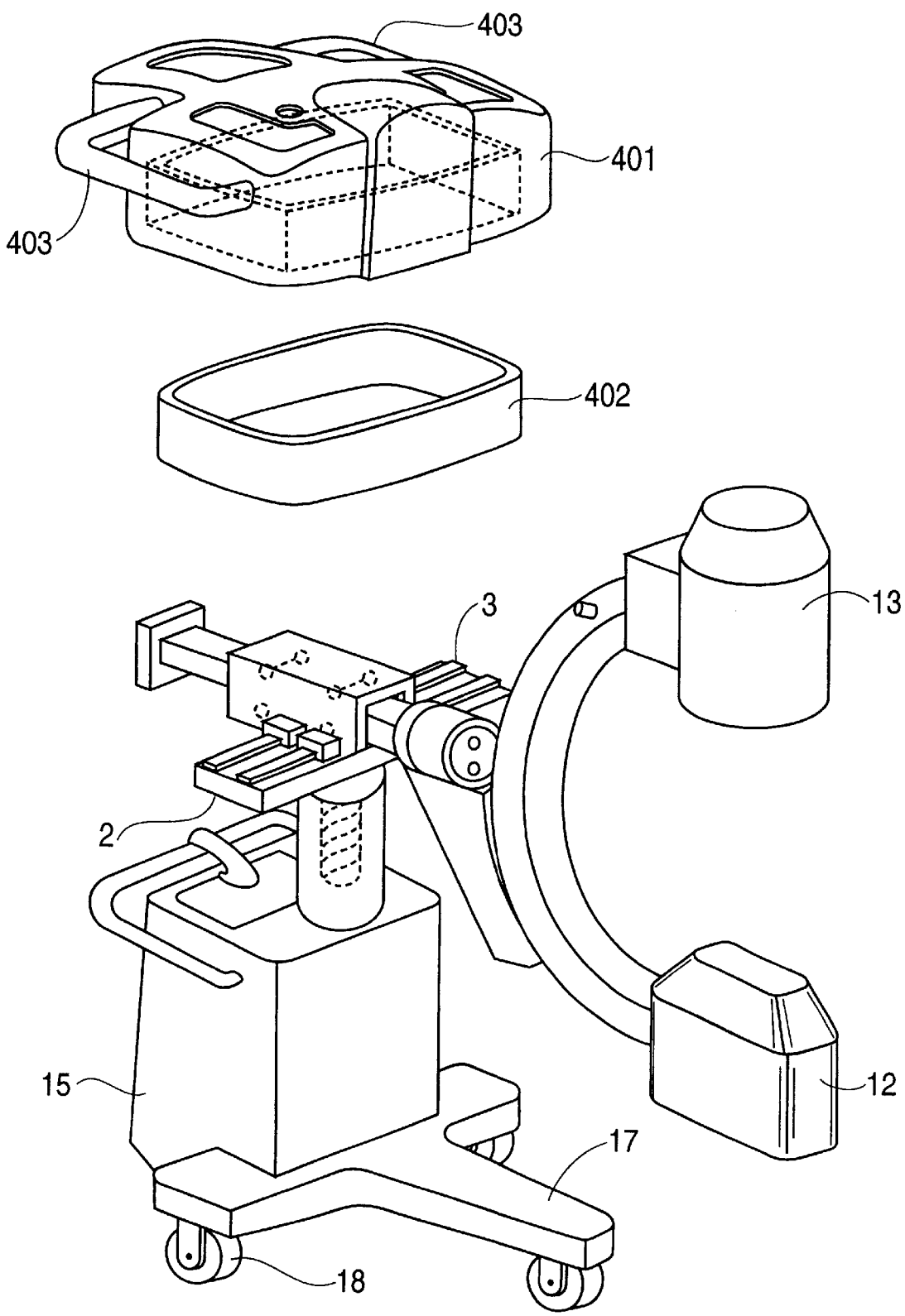
FIG. 6 is a perspective view of a cover covering a top surface of C-arm motion mechanism in an exploded state.
Figure 7D:
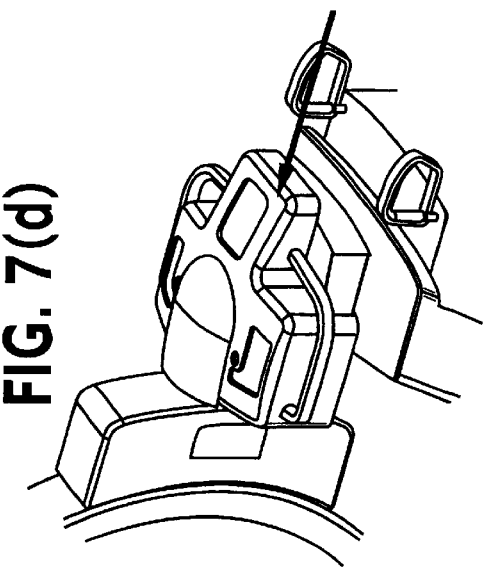
FIG. 7 is a view for explaining a positional relation between a main frame and an operation unit when a C-arm is moved in directions of the top to the bottom, of the left to right, and of the front to the back.
Figure 7B:
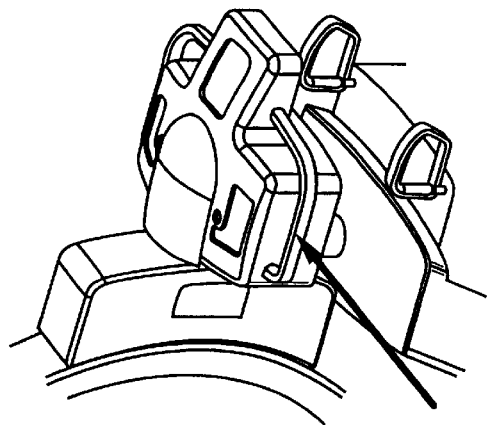
Figure 7C:
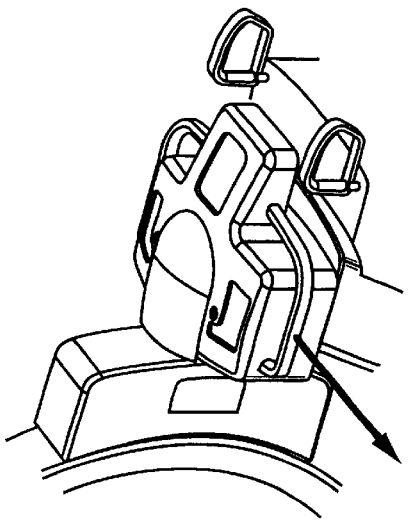
Figure 7A:
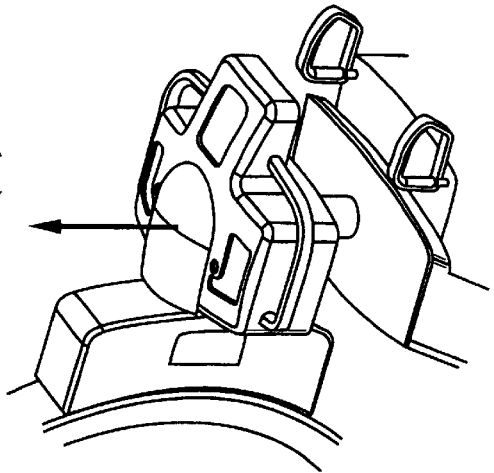

As shown in FIG. 6, a cover for covering registering drive mechanism 100 includes front/back motion cover 401 and left/right motion cover 402 (not shown). Left/right motion cover 402 is integrally combined with front/back motion cover 401 at a position indicated by a broken line inside front/back motion cover 401. Left/right motion cover 402 is fixed so as to support housing 2 of the bearing, engaged with guide rail 3 forming the left/right motion mechanism of registering drive mechanism 100 in the right/left directions. Further, front/back motion cover 401 is fixed so as to support front/back motion shaft 8 forming the front/back motion mechanism of the registering drive mechanism 100, and housing 6 in the front and back direction.

Front/back motion cover 401, on which the operation unit to be described below is mounted on an upper surface thereof, is connected to C-arm supporting portion 10 on its front surface so that a relative location between front/back motion cover 401 and C-arm does not change along with C-arm motion. As shown in FIG. 6, front/back motion cover 401 is supported by the left/right motion mechanism and the front/back motion mechanism inside front/back motion cover 401 so that a relative position between front/back motion cover 401 and up/down main pole 1 can be changed.

Moving truck 17 has brake pedal 601 supported by pedal shaft 602. Brake pedal 601 is provided to fix the X-ray imaging apparatus when it is set to a predetermined position, wherein pedals 601 are symmetrically arranged on the both sides of left and right at the rear part of moving truck 17. When an operator such as a doctor or a technologist steps on brake pedal 601, moving truck 17 is locked and caster 18 of moving truck 17 is also locked to fix the apparatus. When braking pedal 601 is stepped again, the lock is released to enable move of the apparatus. Further, brake pedal 601 has a shape of turning around on sides of moving truck 17 for a purpose of facilitating steps from rear or both sides of the apparatus. Furthermore, brake pedal 601 has, as indicated by a broken line in FIG. 5, a face of bending portion 601', bent at the right angle in the tip thereof inside main frame 15. The face appears from a side of moving truck 17. The face of bending portion 601' is colored by a conspicuous color, different from the colors of main frame 15 or truck 17, for example red or yellow. Thus operator such as a doctor or technologist can easily confirm a state that the entire X-ray imaging apparatus according to the present invention is fixed.

Figure 4A:
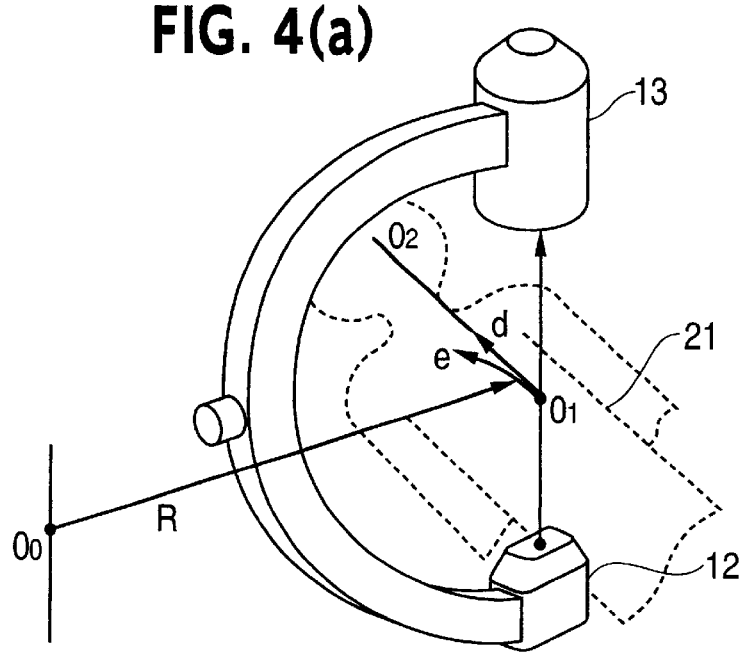
FIG. 4 is a view for explaining a problem caused when a catheter tip is chased by a C-arm swing mechanism.
Figure 4B:
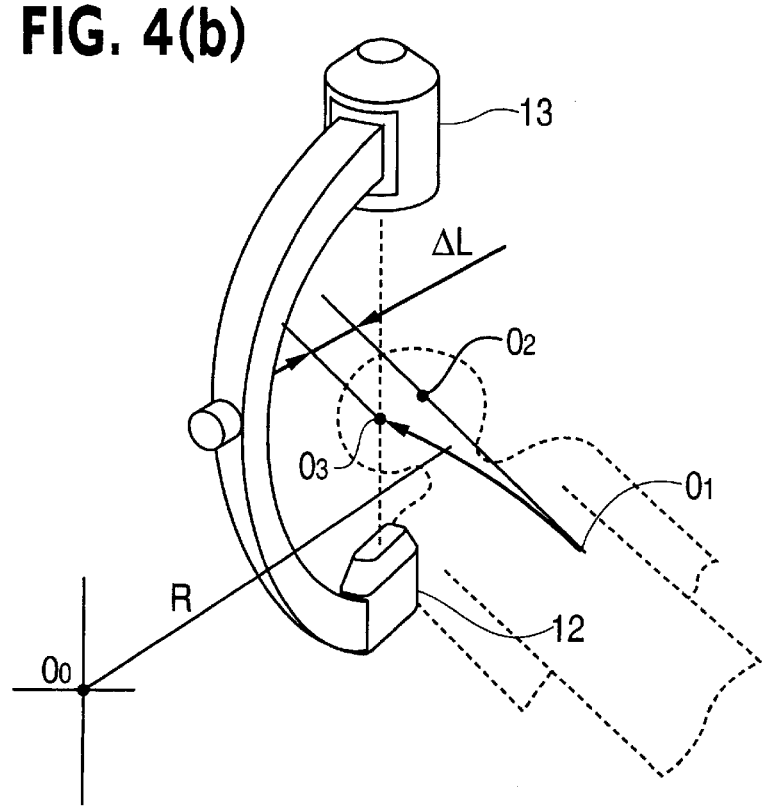

On main frame 15, grips 404 for moving truck is located on the right and left side. Grip 404 is used when a doctor or a technologist moves the entire X-ray imaging apparatus. Because the entire apparatus has a considerable weight, it is hard for a powerless operator to manually move. It is possible to give an electromotive assisting mechanism (not shown) allowing such an operator to easily move the truck for the purpose of facilitating the move. Further, grips 404 may be used only for controlling the moving direction when the truck is completely electromotive. In this case, the electromotive mechanism is controlled by operation buttons located on an operation panel surface to be described below. Further, although the shape of truck motion grip 404 shown in FIG. 5 is different from those shown in FIG. 1 and FIG. 4, wherein its shape can be arbitrarily determined. However, as shown in FIG. 5, if the shape of moving grip 404 is formed in a shape of D, the operator can far more easily grip.

C-arm grips 603 are arranged on left and right sides of C-arm 11 in the vicinity of X-ray tube device 12 and X-ray image reception device 13 for the revolution motion, the circular motion, and the swing motion of the entire C-arm. Thus by locating C-arm grip 603 at the four points on the left and right sides of C-arm in the vicinity of X-ray tube device 12 and X-ray image reception device 13, an operator such as a doctor or a technologist can quickly move the entire C-arm in a desired direction for registration by holding C-arm grip 603 even if the operation is in any position with respect to the X-ray imaging apparatus.

The operation unit is arranged on a top face of front/back motion cover 401. The top face of front/back motion cover 401 is shaped like a spherical surface for the purpose of improving accessibility for the operator to the operation unit from all the directions of front/back, left/right, and top/bottom. Cover 401 has protruding portion 609 projecting to cover a rear end of front/back motion shaft 8 of registering drive mechanism 100, and a central part of the top face has bulge portion 608 covering housing 6 of registering drive mechanism 100.

The operation unit located on the top face of front/back motion cover 401 includes control panel 605 respectively having a plurality of control buttons on the left and right sides of bulge portion 608, two emergency buttons 610 located at positions in the vicinity of these control panel 605, and operation panel 606 located at protruding portion 609. The space among front/back motion cover 401 having the operation part and C-arm supporting portion 10 for supporting C-arm 11 and horizontal rotation shaft 9 is covered with supporting part cover 604 to connect these. On both sides of supporting cover 604, control panel 607 having C-arm moving operation button the same as the control button located in control panel 605, is disposed. Operation panel 607 is disposed so that a doctor or a technologist can do operation the same as those in operation panel 605 even when the operator is on a side of a subject but is apart from operation panel 605. Moreover, on the top face of main frame 15 and on left and right sides thereof, rise control button 611 and fall control button 612 are located for controlling rising up and falling down of the C-arm. Arrangement and functions of operation buttons arranged the operation panel 605–607, wherein the function of said rise control button 611 and fall control button 612 will be described later. In the X-ray imaging apparatus according to the embodiment of the present invention described above, as the operation portion for controlling the traveling of C-arm is located on the top face of front/back motion cover 401, of which relative position with respect to the supporting portion of C-arm 11 does not change, the operation unit is always positioned at a predetermined distance from the supporting portion of C-arm as a base point, whereby the doctor or the technologist can easily control.

On the both side faces of front/back motion cover 401, C-arm motion grip 403 is located so as to turn from a front part of the cover to the side face of protruding portion 609 such that C-arm motion grips 403 can be easily grasped. This C-arm motion grips 403 are used for the vertical motion, the front/back motion, and the left/right motion of the C-arm. If grips 403 are used to move the entire apparatus without locking a brake of truck, all power for moving the entire apparatus is applied to main pole 1 in the lateral direction. By grasping C-arm motion grip 403 and applying force in a desirable direction among top/bottom, front/back, and left/right directions, C-arm 11 moves in the desirable direction. As previously described, it is possible to add the electromotive assisting mechanism to substitute a completely electromotive mechanism for the grip to enable control by operation button in an operation panel.

In reference of FIG. 7, a positional relationship between the operation unit and the main frame will be described in a case where the entire C-arm is moved in the directions of top/bottom, left/right, front/back. FIG. 7(*a*) shows a state that the entire C-arm is upwardly moved. When main pole 1 ascends, front/back motion cover 401 provided with the operation unit is raised up, whereby the space between a bottom face of front/back motion cover 401 and main frame 15 is increased to expose main pole 1. The vertical motion is performed by the C-arm vertical motion mechanism, and the maximum distance of vertical motion is set about 410 mm. The vertical motion distance is set an appropriate value in response to the height of a subject on a bed, a distance between the subject and an X-ray tube focus point of X-ray tube device, and distance between the object and an X-ray image reception device, and so on at each time of use.

FIG. 7(*b*) shows a state that the entire C-arm is moved from the state shown in FIG. 7(*a*) in the direction of arrow, i.e. the right direction when an operator stands against the C-arm. In this case, a position of main pole 1 with respect to the top face of main frame 15 does not change, and front/back motion cover 401 moves in the right direction along with C-arm, whereby a left half of the top face of main frame 15 is exposed. FIG. 7(*c*) shows a state that the entire C-arm is leftward moved under a state that the entire C-arm is positioned at the lowest position. Such a left/right motion is performed by the C-arm left/right motion mechanism, wherein the maximum distance of left/right motion is about 350 mm. In other wards, the distance is ±75 mm with respect to an intermediate position of the left/right motion.

FIG. 7(*d*) shows a state that the entire C-arm is forwardly moved. The front/back motion is performed from any condition shown in FIG. 7(*a*) to FIG. 7(*c*), and performed by the C-arm front/back motion mechanism. The maximum distance of this front/back motion is set about 200 mm.

Figure 8:
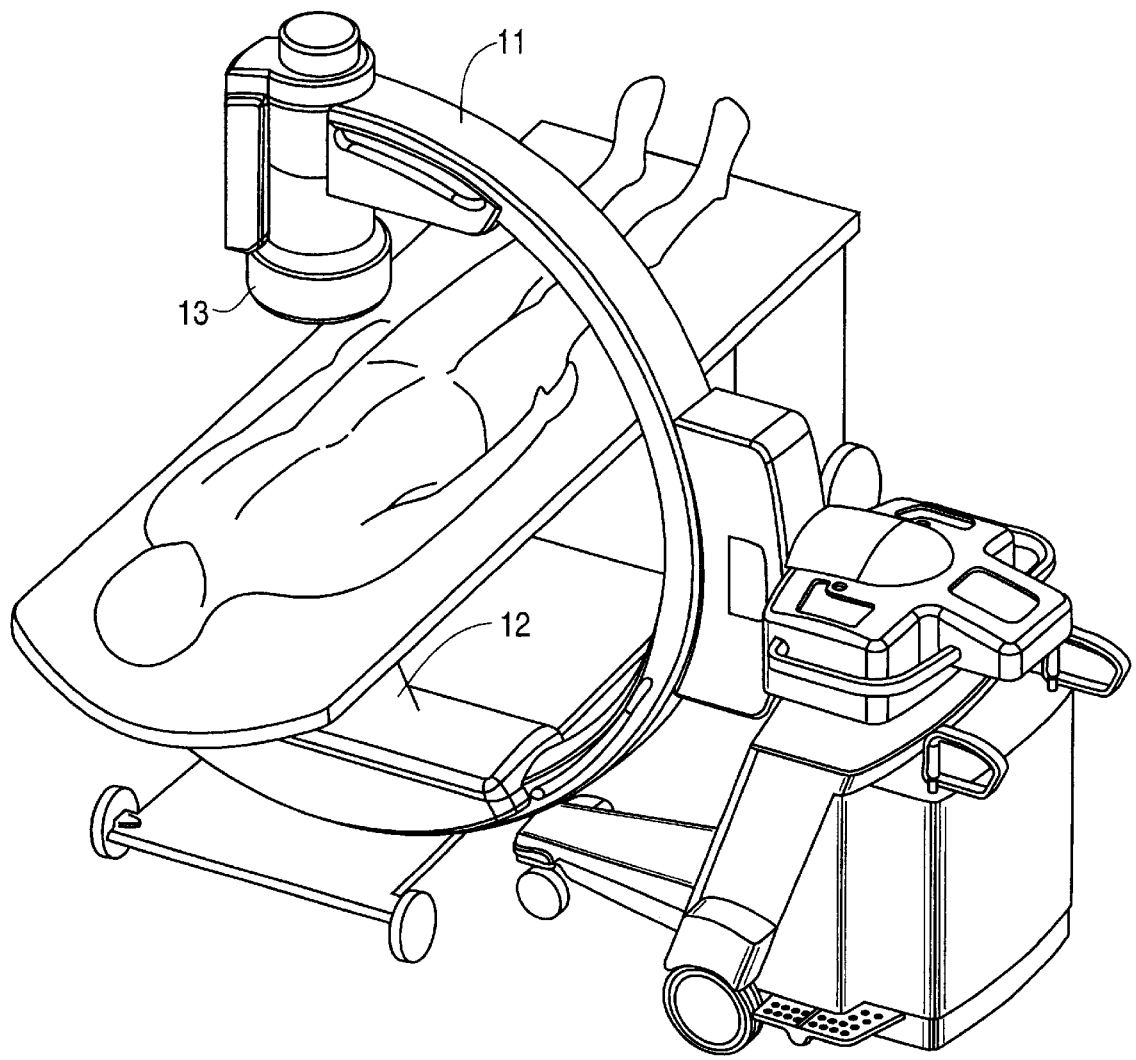
FIG. 8 is a perspective view for explaining a positional relation among a mobile type radiography apparatus, a bed, and a subject to be examined.

Next, the revolution motion, the circular motion, and the swing motion of C-arm will be described. Because these motions are performed by the above-described mechanisms, it will be described in reference of FIG. 8. The revolution motion is performed by the revolution mechanism explained above. In the example shown in FIG. 8, the revolution motion is used for the purpose of introducing an X-ray flux irradiated from X-ray tube device 12 to X-ray image reception device 13 installed on the C-arm in an oblique direction with respect to the subject on the surface including the body axis of the subject. In the example shown in the figure, it is possible to revolve the C-arm until the position where the X-ray tube device 12 is in contact with the subject or X-ray image reception device 13 is in contact with the bottom face of the bed.

When the C-arm is moved so that X-ray imaging apparatus is positioned on the head side of the subject, the C-arm can be revolved at the position where X-ray tube device 12 and X-ray image reception device 13 are positioned on the both sides of bed and the X-ray tube device reaches under the bed. Thus a flux of X-ray can be irradiated in various directions, for example, from a side, or from a top or a bottom to the head of the subject. To realize these modes of use, in the present invention, the C-arm can be revolved by an angle of about 280 degrees in the clockwise direction (or the counterclockwise direction) and an angle 100 degrees in the reverse direction thereof when an operator views the C-arm on the side of operation unit under a state that the X-ray tube is in the uppermost position. Thus, a range of about 380 degrees can be totally covered in the revolution direction, whereby overlapping organs and vessels in a subject can be observed by fluoroscopic imaging or radiographic imaging.

The swing motion is to swing the entire C-arm in the horizontal direction of left/right around the center shaft of main pole 1, wherein the swing motion is effectuated by the above-described C-arm swing motion mechanism. Because, in the present invention, the swing motion is an aid of the left/right motion, it is unnecessary to provide a large swing angle, and a small swing angle is sufficient. If the swing angle is increased, there is a danger that stability of the truck is lost. However, as in the present invention, by adding the left/right motion of the C-arm to reduce the swing, there is a merit that anti-falling stability of the apparatus is enhanced.

Figure 9:
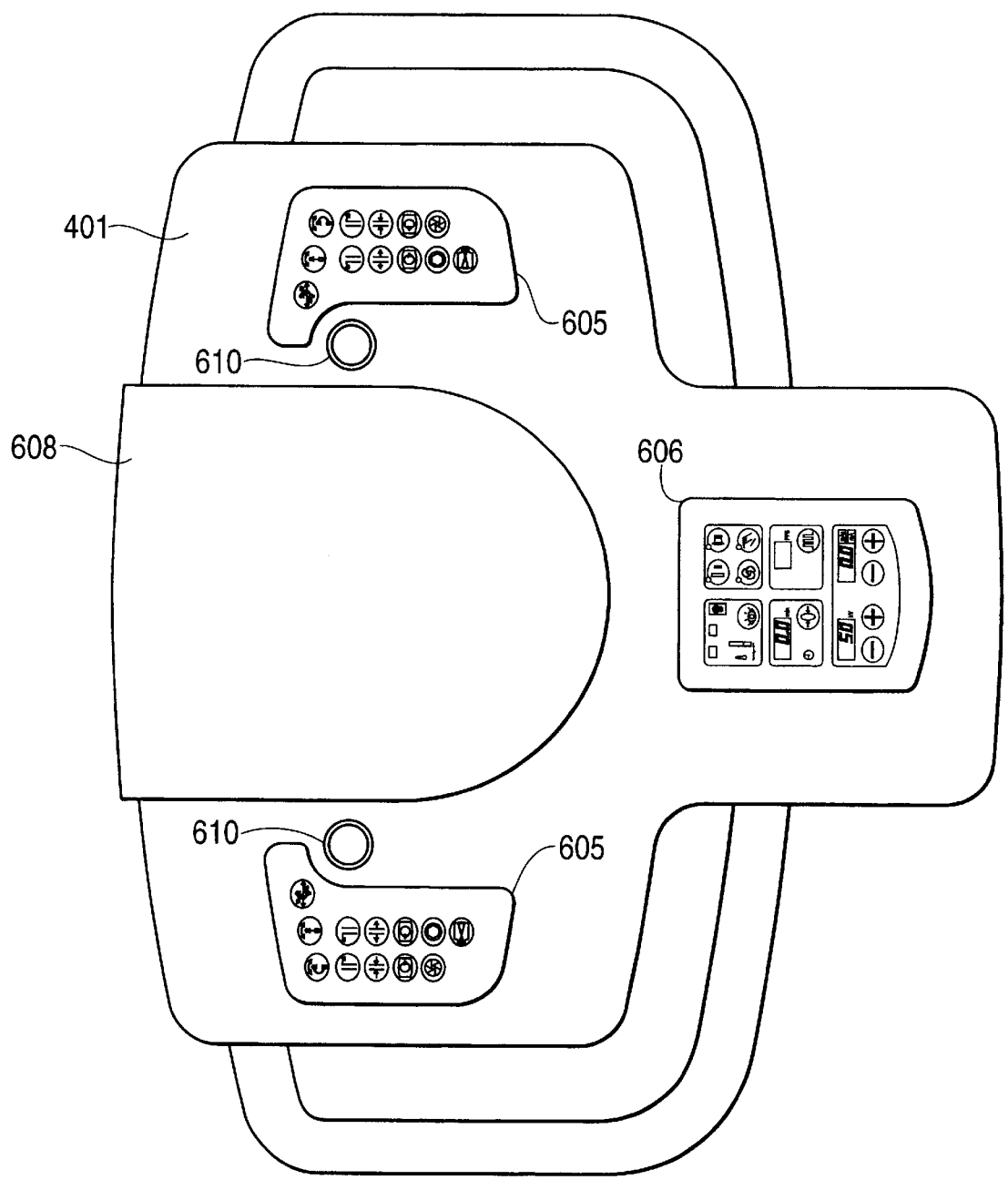
FIG. 9 is a view for explaining an arrangement of an operation panel in an operation unit.

Next, the operation panel in the operation unit will be described. FIG. 9 is a drawing showing an arrangement of the operation panel on the top face of front/back motion cover 401. Further, FIGS. 10–12 explain an arrangement of the control buttons in the operation panel. In the control panel described below, no control button for the C-arm swing motion is provided. This is because a case where the exemplified as the premise. Therefore, if it is judged that a swing mechanism is indispensable in constructing an apparatus, an operation button for the swing mechanism may be provided in its operation panel.

The control unit disposed on the top face of front/back motion cover 401 includes operation panels 605 respectively having a plurality of operation buttons and symmetrically disposed left and of bulge portion 608 of cover 401, emergency button 610 for stopping function of the entire apparatus in case of emergency, and operation panel 606 disposed on protruding portion 609 of cover 401. In operation panels 605, operation buttons for driving the C-arm and operation buttons for controlling the state of X-ray image reception device 13 are provided. In the operation panel 606 disposed in protruding portion 609, operation buttons for controlling the state of X-ray tube device 12 and a display portion for displaying the state of X-ray tube device 12 are disposed.

Figure 10:
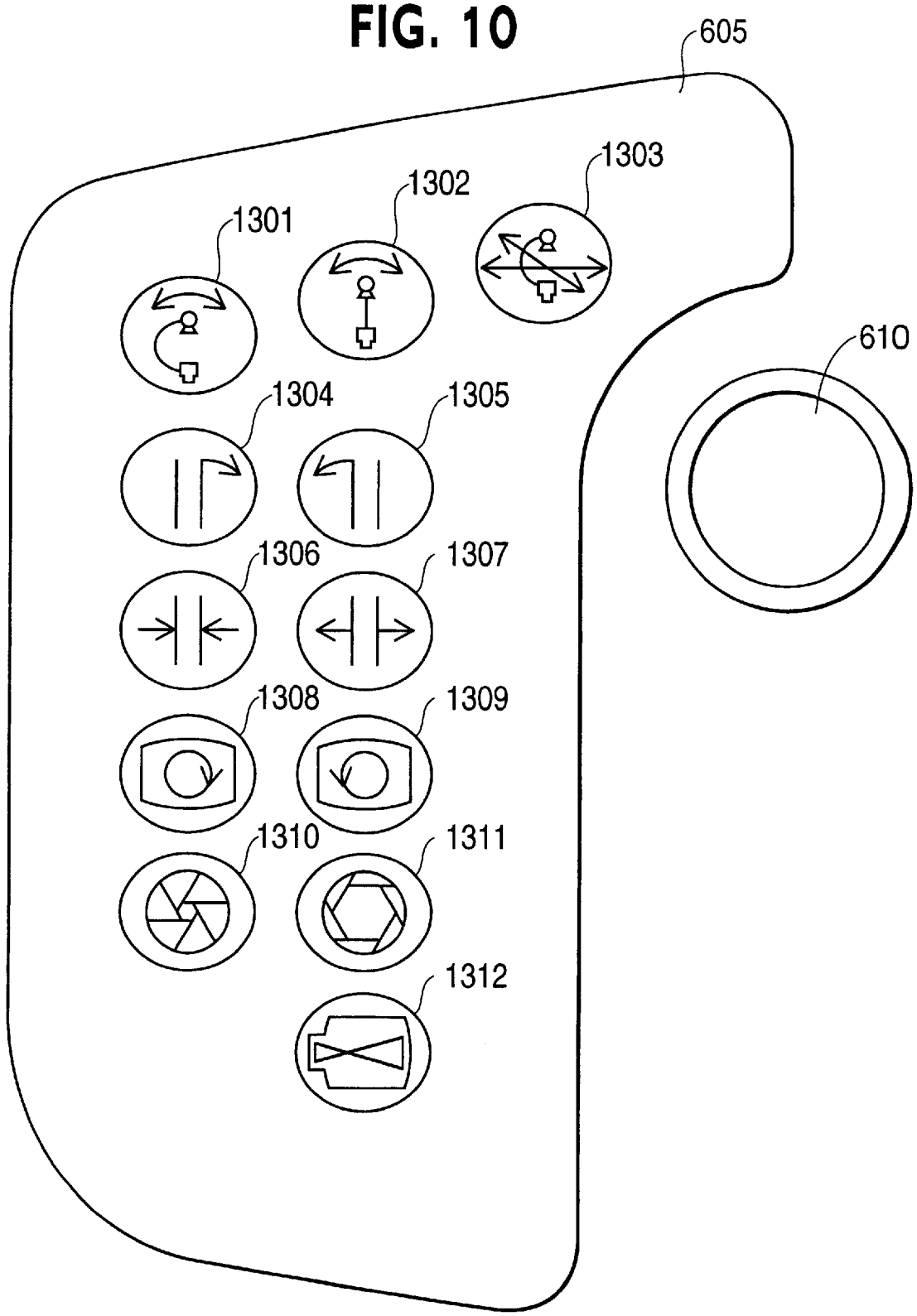
FIG. 10 is a view for explaining an arrangement placement and a display of operation buttons in symmetrically arranged operation panel portions on the panel shown in FIG. 9.

FIG. 10 is an enlarged view of the operation panel and the emergency button in the lower part of FIG. 9 showing the operation panels. Buttons 1301 to 1303 are provided for locking and unlocking traveling of C-arm 11, the buttons being respectively for the circular motion, the revolution motion, the front/back motion, and the left/right motion. When these buttons are repeatedly pushed, the locked and unlocked states are repeated. The C-arm is freed from the motion mechanism allocated to the button when that button is unlocked. The C-arm is electro-magnetically locked with respect to the motion mechanism allocated to the button when that button is locked. In this case, the front/back motion, the left/right motion, and the revolution motion, circular motion are manually performed or done so with electromotive assistance, and only the vertical motion is electro-motively performed.

Buttons 1304 and 1305 are to rotate blades of X-ray aperture device (X-ray collimator) located inside X-ray tube device 12. While the buttons are pushed, the collimator blades are rotated in the direction of arrow, displayed on the button. Buttons 1306 and 1307 are to close and open the collimator blades. Button 1306 is for "closing", and button 1307 is for "opening". Buttons 1308 and 1309 are to control the rotation of an examination image displayed on an image display (not shown), wherein while the buttons are pushed, the display image is rotated in the direction of arrow displayed on the button. Buttons 1310 and 1311 are iris buttons, wherein button 1310 is for "closing", and button 1311 is for "opening". During the buttons are pushed, the iris continuously moves. Button 1312 is a zoom button having a function of changing a field of view.

Operation panel 606 located on bulge portion 609 is for displaying and controlling a state of X-ray tube device 12. As shown in FIG. 11, a display lamp, an operation button and so on are disposed in parts A to E. In part A, power supply lamp 1401 lighting while power is thrown in the apparatus, and ready lamp 1402 (lamp indicating ready for X-ray irradiation) for indicating that X-ray irradiation is possible by normally lighting 5 seconds after throwing in power, X-ray irradiation lamp 1403. lighting during an X-ray is irradiated (continuously lighting in fluoroscopy by X-ray pulse irradiation), temperature display device 1404 for displaying a temperature of the X-ray tube, fluoroscopy button 1405 for performing fluoroscopy when indirect (DR) technique is selected, are disposed.

Part B includes fluoroscopy integrating time display unit 1406 enabling digital display of an integration time of fluoroscopy in a unit of 0.1 minute and fluoroscopy integrated time resetting button 1407. Fluoroscopy integrated time resetting button 1407 is provided to clear the integrated time and stops an alarm buzzer, whereby continuously pushing it, an integrated irradiation time after throwing power in is displayed, and by further continuously pushing it, the integrated irradiation time is cleared.

Part C includes direct photographic technique selecting button 1408 for imaging with an X-ray irradiation by operating a hand-held switch without a DR connection (when this is selected, the X-ray condition is controlled in mAs), indirect photographic technique selecting button 1409 for performing indirect photography (the exposure time is constant) by irradiating an X-ray with a DR foot switch, auto fluoroscopy selecting button 1410 for automatically adjusting the tube voltage by a KIBS signal from DRS, and manual fluoroscopy selecting button 1411 for manually setting the tube voltage for fluoroscopy.

Part D includes pulse fluoroscopy display device 1412 for displaying a pulse fluoroscopy rate, fluoroscopic mode selection button 1413 for cyclically changing over among "fluoroscopy", "pulse fluoroscopy", and "boost fluoroscopy" on each push of the button. The pulse fluoroscopy rate is changed with a fluoroscopy tube current setting button to be described later.

Part E includes tube voltage display device 14 for displaying the voltage of X-ray tube, tube voltage setting device 1416 for increasing and decreasing the tube voltage by a unit of 1 kV and continuously switching over (auto-repeating) its value when the button is stationarily pushed, fluoroscopy tube current/mAs display device 1417 for displaying tube currents in fluoroscopy, pulse fluoroscopy and radiography, and fluoroscopy tube current/mAs setting button 1418 for increasing and decreasing the tube current and a pulse ratio.

Next, operation panel 607 arranged on a side of cover 604 of the C-arm supporting portion will be described. As shown in FIG. 12, operation buttons of C-arm 11 are located in operation panel 607. FIG. 12(a) shows operation panel 607 when the C-arm is in an ordinary state (X-ray tube device 12 is on a top side). FIG. 12(b) shows operation panel 607 when the C-arm is reversed and X-ray tube device 12 is on a bottom side. Among operation buttons in operation panel 607, buttons 1301–1303 have the same functions as those described in reference of FIG. 10. In addition to these buttons, operation panel 607 has operation buttons 1501 and 1502 for controlling ascent and descent of the C-arm. On operation buttons 1501 and 1502, not only the main body, the truck and the C-arm but also arrows indicating moving direction are illustrated. The above-mentioned emergency button may be located in an inside of or in a periphery of operation panel 607.

Since on the surface of the buttons disposed to the operation panels described above, illustrations showing the functions of the buttons are printed, erroneous control is prevented.

According to the embodiment of the present invention, since a plurality of operation panels are disposed on an upper portion of the C-arm motion, and the operation panel is disposed in the C-arm supporting portion, a doctor or a technologist or the like, who is performing an IVR method by a subject on a bed can easily move the C-arm, control the X-ray collimator, and control the iris of the X-ray image reception device.

Figure 15:
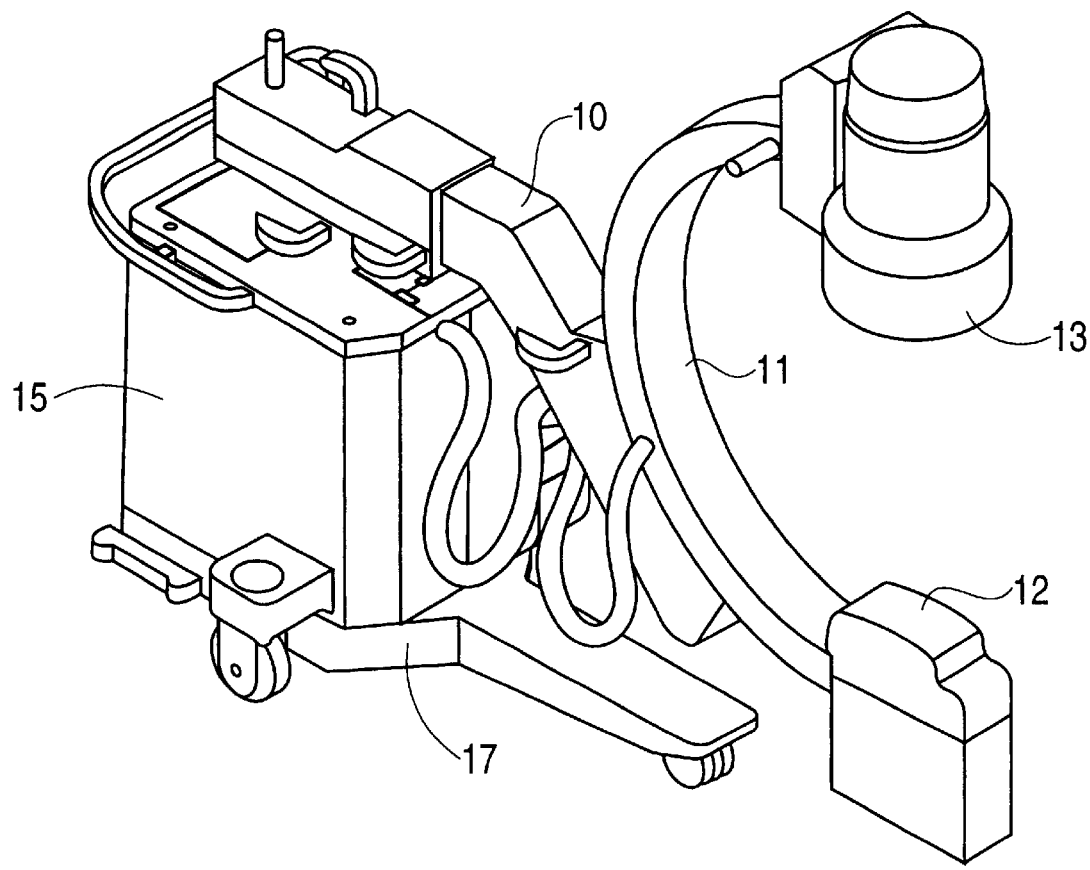
FIG. 15 is a view for illustrating a cable handling mechanism in the conventional mobile type radiography apparatus.

Next, a mechanism for handling cables connected to X-ray tube device 12 and to X-ray image reception device 13 according to the present invention will be described. As previously described, in the conventional mobile type radiography apparatus, the cables are connected to the X-ray controlling portion in the main body from X-ray tube device 12 and X-ray image reception device 13 shown in FIG. 15 through the interior of C-arm 11 after drawing outside C-arm 11 at around a middle between the both ends of C-arm 11, slacking a length corresponding to a motion of C-arm 11, and temporally fixing to the C-arm supporting portion. However, a high voltage cable connected to X-ray tube device 12 is big and hard. Therefore, when a cable connected to X-ray image reception device 13 is bundled up with the high voltage cable, the C-arm us prevented from freely moving; the cables are apt to dirty by touching on a floor of operating room; and the cables sometimes impede a doctor, a technologist, or the like by occupying his or her standing positions.

Technical solutions to the problems are disclosed Japanese Unexamined Utility Model Publication JP-A-4-98835 and Japanese Unexamined Patent Publication PA-A-6-70918. In the cable handling mechanisms described above, a cable connected to an X-ray image reception device is detoured on a side of X-ray tube device toward an X-ray image reception device. Although the above problem can be solved by this cable handling mechanism, it is further necessary to prevent noise generated by a high voltage applied to an X-ray tube from emerging in an X-ray image. In the embodiment of the present invention, it is possible to realize a cable handling mechanism, which is free from the above problem and influence of noise on an image generated by a high voltage.

Figure 13:
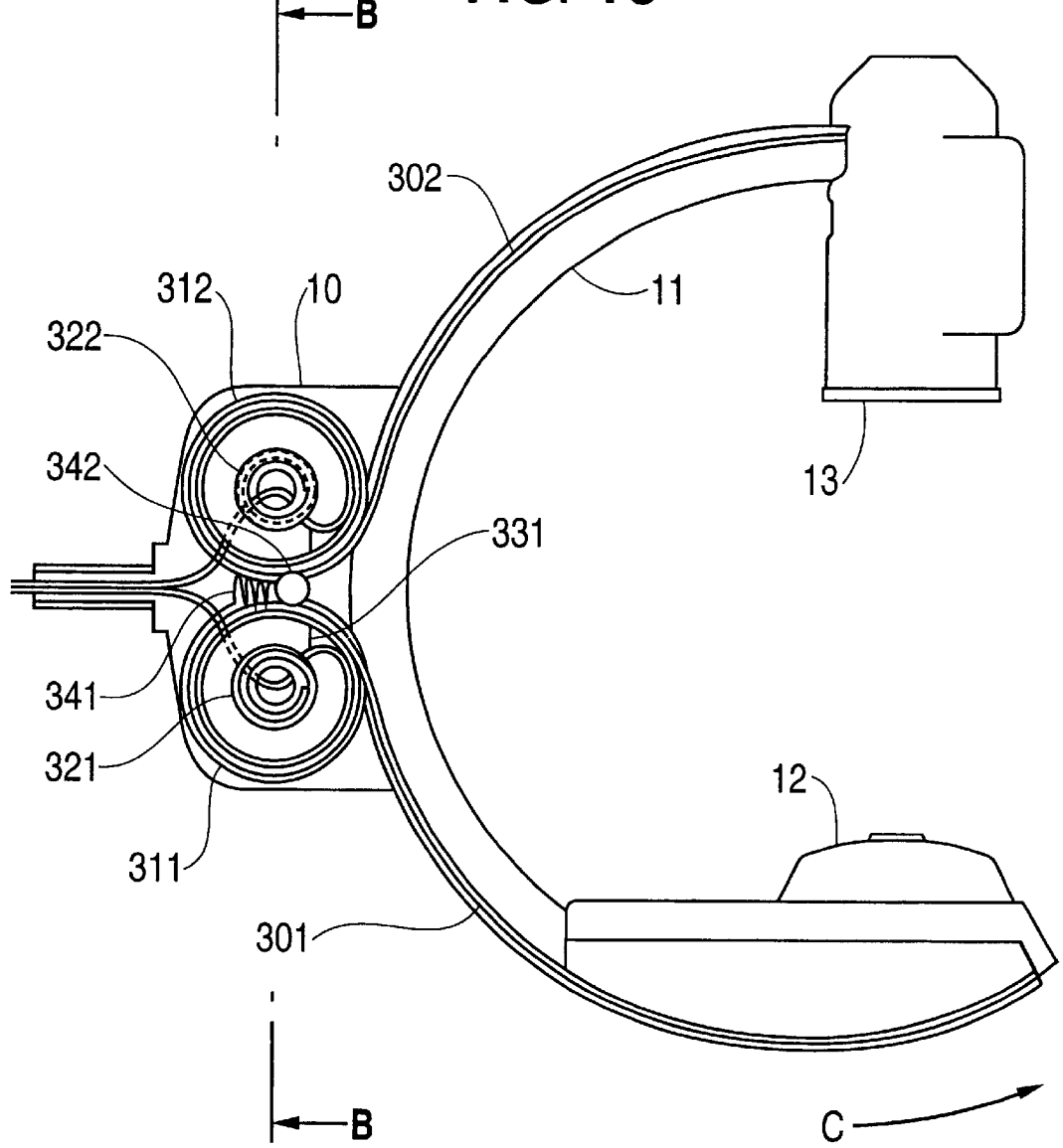
FIG. 13 is a view for explaining entire composition of a cable handling mechanism of a mobile type radiography apparatus according to the embodiment of the present invention.

Hereinafter a cable handling mechanism for a mobile type radiography apparatus according to the present invention will be described. FIG. 13 illustrates an entire C-arm supported by C-arm supporting portion 10 and a cable winding mechanism of the cable handling mechanism.

In this apparatus, a cable for X-ray tube device 12 and a cable for X-ray image reception device are guided directly into C-arm supporting portion 10 through C-arm 11. Therefore, it is unnecessary to route the cable from one side of C-arm 11 to the other side. In C-arm supporting part 10, a pair of winding mechanisms is built-in.

The winding mechanisms respectively include winding drum 311 or 312 for winding cable 301 or 302, spiral pulley 321 or 322 coaxially attached to drum 311, 312. In reference of FIG. 14, i.e. a cross-sectional view taken along line A—A in FIG. 13, winding drums 311, 312 are a flat type including winding drum, flanges 314 at both ends thereof and a hollow rotation shaft 315. Winding drum 313 is partly notched (not shown) to enable insertion of cable 301, 302 through the notch. In addition, spiral pulleys 321 and 322 are in a truncated cone shape, and are coaxially fixed respectively to drum 311,312, wherein on the truncated faces, spiral groove 323 is formed. In this figure, one side of spiral pulleys 321 and 322 has a smaller radius, the other side has a larger radius. Spiral pulley 321 is arranged so that the large-diameter side is directed to drum 311, spiral pulley 322 is arranged so that the small-diameter side is directed to drum 311. Wire rope 331 is wound around both of spiral pulleys 311,312, so that these are interlocked.

Cable 301 to X-ray tube device 12 is wound around drum 313 of winding drum 311 by several times. Cable 302 for X-ray image reception device 13 is wound around drum 313 of winding drum 312 by several times. The cables are respectively introduced into an inside of winding drum through the notch the drum, wound around the circumference of rotating shaft 315 by several times, drawn into an inside of the rotating shaft through an insertion hole formed in rotation shaft 315, bundled, and transferred to the X-ray control unit.

When cable 301 to X-ray tube device 12 is pulled out in the direction of B (counterclockwise direction) in FIG. 13 by the circular motion of C-arm 11, drum 311 is rotated in the clockwise direction; drum 312 is interlocked with drum 311 to rotate in the clockwise direction for winding and cable 302 to X-ray image reception device 13. At this time, the outer diameter of drum 311 including the cable becomes thinner by drawing out the cable. On the other hand, the outer diameter of drum 312 including the cable becomes thicker by winding the cable. Therefore, the spiral pulleys are mutually arranged on the opposite sides. Provided that the equation of D1:D=D3:D4 is established in designing the cable handling mechanism, where D1 represents the radius of the spiral pulley; D2 represents the diameter of wire rope 331; D3 represents the diameter of the winding drum; and D4 represents the diameter of the cable, a pair of the drums are relatively easily synchronized.

Figure 14:
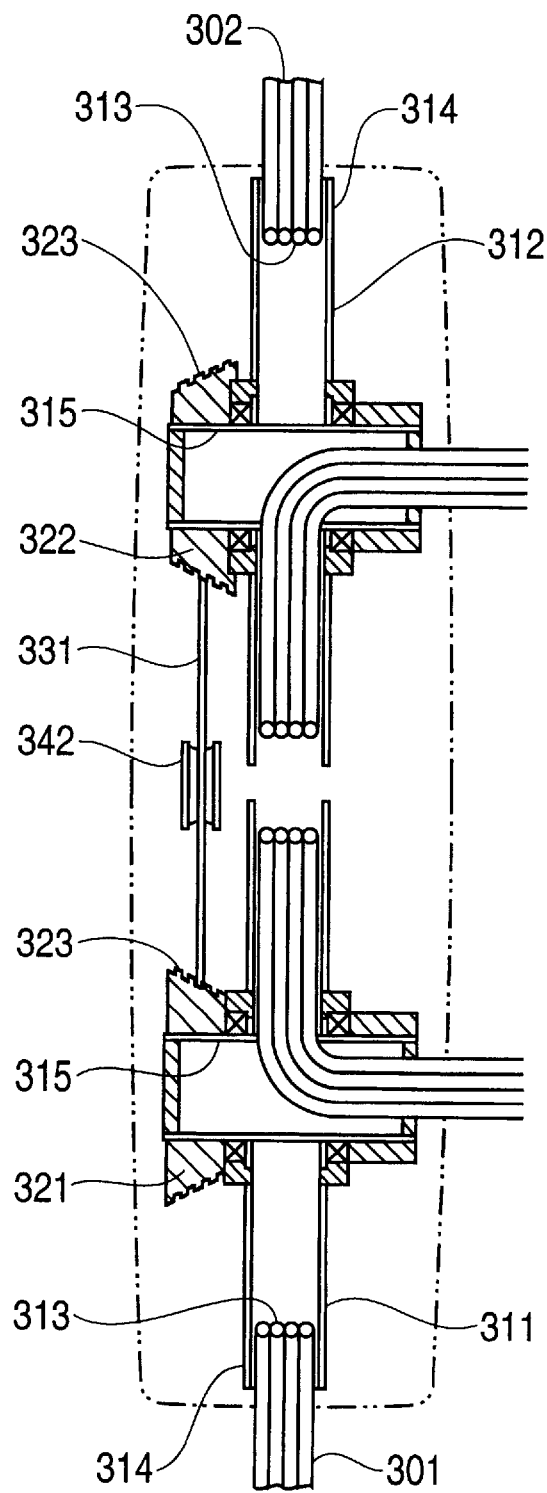
FIG. 14 is a cross-sectional view taken along line B—B in FIG. 13.

Meanwhile, it is necessary to assemble the components of the cable handling mechanism carefully because there is a possibility of causing a small synchronization error by an assembling error or the like. Slack of wire rope 331 being one reason of the synchronization error, can always be removed by using spring 341 and pulley 342 as shown in FIGS. 13 and 14.

As described above, according to the embodiment of the present invention, the cable to the X-ray tube device and the cable to X-ray image reception device are built in the C-arm, whereby the appearance of the apparatus is improved; cleanliness of the cables is maintained; and the cables do not prevent work of a doctor or the like. Further, because the cables are directly wired from a center portion of the C-arm to the respective connecting points, noise caused by a high voltage scarcely applied to the cable to X-ray image reception device, whereby a good X-ray image is obtained.

Although the preferred embodiment according to the present invention has been described, it is needless to say that various modifications are applicable in light of the scope of the present invention.

What is claimed is:

1. A mobile type radiography apparatus comprising;
   a truck movable on a floor;
   an X-ray control unit mounted on said truck;
   a first supporting arm having two branches supporting an X-ray generator and an X-ray image reception device at mutually opposite positions to sandwich a subject between said X-ray generator and said X-ray image reception device;
   an arm supporting mechanism having a second arm extending toward an outside of the branches of said first supporting arm and supporting said first supporting arm so as to be movable;
   a supporting pole mechanism mounted on said truck so as to extend upwardly therefrom; and
   an arm motion mechanism located between said arm supporting mechanism and said supporting pole mechanism for linearly supporting said arm supporting mechanism so as to enable movement of said first supporting arm in horizontal directions perpendicular to longitudinal directions of said second arm.

2. A mobile type radiography apparatus according to claim 1, wherein said first supporting arm has a shape of a C and is a C-arm.

3. A mobile type radiography apparatus according to claim 2, wherein said arm supporting mechanism comprises a C-arm circular motion mechanism for moving said C-arm in circular directions of said C-arm and a C-arm revolution mechanism for rotating said C-arm around a center axis of said second arm.

4. A mobile type radiography apparatus according to claim 3, wherein said arm supporting mechanism further comprises a C-arm front/back motion mechanism for moving said second arm in directions along a center axis thereof.

5. A mobile type radiography apparatus according to claim 1, wherein said supporting pole mechanism comprises a vertical motion mechanism for moving said C-arm in vertical directions.

6. A mobile type radiography apparatus according to claim 1, wherein a stroke of said arm motion mechanism is 350 mm.

7. A mobile radiography device comprising:
   a truck movable on a floor;
   a first supporting arm having two branches supporting an X-ray generator and an X-ray image reception device at mutually opposite positions to sandwich a subject between said X-ray generator and said X-ray image reception device;
   an arm supporting mechanism having a second arm extending toward an outside of the branches of said first supporting arm and supporting said first supporting arm so as to be movable;
   a supporting pole mechanism mounted on said truck to extend upwardly therefrom; and an arm motion mechanism located between said arm supporting mechanism and said supporting pole mechanism and movably supporting said arm supporting mechanism in horizontal directions perpendicular to longitudinal directions of said second arm so as to enable movement of said arm supporting mechanism in the horizontal directions;

a main body mounted on said truck and having an X-ray control unit therein; and an operation unit located over said arm motion mechanism to cover said arm motion mechanism, said operation unit having a plurality of operation panels.

8. A mobile type radiography apparatus according to claim 7, wherein said operation unit has two operation panels having common functions to enable operation on both sides of said supporting arm.

9. A mobile type radiography apparatus according to claim 7, wherein said operation unit has at least one operation panel having an operation device for controlling motion of said arm motion mechanism.

10. A mobile type radiography apparatus according to claim 9, wherein said operation device disposed in said operation panel has a mark showing a moving direction of said first supporting arm.

11. A mobile type radiography apparatus according to claim 7, wherein said main body has a traveling grip in a traveling direction of said truck, and said operation unit has an operation panel located therein so as to enable operation at a traveled position of said truck.

12. A mobile type radiography apparatus comprising:

a truck movable on a floor;

an X-ray control unit being mounted on said truck;

a first arm having a shape of a C which is a C-arm and supporting an X-ray generator and an X-ray image reception device at mutually opposite positions to sandwich a subject between said X-ray generator and said X-ray image reception device;

a C-arm supporting mechanism having a second arm extending toward an outside of said C-arm and supporting said C-arm so as to be movable;

a supporting pole mechanism mounted on said truck to extend upwardly therefrom; and a C-arm motion mechanism located between said C-arm supporting mechanism and said pole supporting mechanism, and movably supporting said C-arm supporting mechanism in horizontal directions perpendicular to longitudinal directions of said second arm so as to enable movement of said C-arm supporting mechanism in the horizontal direction; and a cable handling mechanism located in a C-arm supporting portion of said C-arm supporting mechanism for winding one of cables, the cables being connected from said X-ray control unit respectively to said X-ray generator and to said X-ray image reception device, and for drawing out another cable in response to a circular motion of said C-arm.

13. A mobile type radiography apparatus according to claim 12, wherein said cables extending from said X-ray generator and said X-ray image reception device to said cable handling mechanism are wired along said C-arm and are directly inserted in said cable handling mechanism.

14. A mobile type radiography apparatus according to claim 12, wherein said cable handling mechanism has a pair of cable winding drums respectively corresponding to said cables, a plurality of grooves are formed on circumferences of said drums for winding said cables, said drums are rotatably supported by a hollow shaft, and said cables are introduced from circumferences of said drums to an inside of said hollow shaft so that circumference sides are connected to said X-ray generator and said X-ray image reception device.

15. A mobile type radiography apparatus according to claim 14, wherein the diameters of said grooves formed in said winding drums gradually change in an axis direction of said drums.

16. A mobile type radiography apparatus according to claim 14, wherein said pair of cable winding drums are rotated so that a cable winding amount of one of said cables and a cable drawing amount of another cable are the same.

17. A mobile type radiography apparatus according to claim 16, wherein said pair of cable winding drums are interlocked to be rotated in a common direction at a common rate when said C-arm is subjected to a circular motion.

* * * * *